(12) United States Patent
Rezgui et al.

(10) Patent No.: US 7,832,501 B2
(45) Date of Patent: Nov. 16, 2010

(54) MEASUREMENT AHEAD OF THE DRILLING BIT BY ANALYSIS OF FORMATION CUTTINGS USING ULTRAVIOLET LIGHT TO DETECT THE PRESENCE OF OIL OR GAS

(75) Inventors: Fadhel Rezgui, Chatillon (FR); Stéphane Vannuffelen, Meudon (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 103 days.

(21) Appl. No.: 11/863,336

(22) Filed: Sep. 28, 2007

(65) Prior Publication Data
US 2009/0095529 A1  Apr. 16, 2009

(30) Foreign Application Priority Data
Oct. 9, 2006  (EP) ............................ 06291592

(51) Int. Cl.
*E21B 47/00* (2006.01)
(52) U.S. Cl. .......................... 175/40; 175/41
(58) Field of Classification Search ............ 175/41, 175/40, 50, 57; 73/152.19; 250/254
See application file for complete search history.

(56) References Cited

U.S. PATENT DOCUMENTS

| 4,297,880 | A | * | 11/1981 | Berger | ............... 73/152.22 |
| 4,609,821 | A | | 9/1986 | Summers | |
| 5,061,849 | A | * | 10/1991 | Meisner et al. | ............. 250/254 |
| 5,084,617 | A | | 1/1992 | Gergely | |
| 6,176,323 | B1 | | 1/2001 | Weirich et al. | |
| 2007/0137293 | A1 | * | 6/2007 | Pop et al. | ................. 73/152.23 |

FOREIGN PATENT DOCUMENTS

GB  2 389 380  12/2007

* cited by examiner

*Primary Examiner*—William P Neuder
(74) *Attorney, Agent, or Firm*—Dave R. Hofman

(57) ABSTRACT

An apparatus for determining the nature of the formation at the bottom of a wellbore being drilled with a tubular drill string through which drilling fluid is pumped to return the drilling fluid to the surface via the wellbore, the apparatus comprising a tool body for installation in a drill string with a bore extending there through and an ultraviolet fluorescence detector in a passageway in the tool body, the tool body being configured to receive drilling fluid from inside the drill string and to receive drilling fluid from outside the drill string, wherein the drilling fluid can be directed past the detector so as to enable measurements to be made.

11 Claims, 1 Drawing Sheet

MEASUREMENT AHEAD OF THE DRILLING BIT BY ANALYSIS OF FORMATION CUTTINGS USING ULTRAVIOLET LIGHT TO DETECT THE PRESENCE OF OIL OR GAS

BACKGROUND OF THE INVENTION

1. Field of the Invention

The invention relates to apparatus and methods for determining the nature of formations at the bottom of a wellbore for use in the oil and gas industry. More specifically the invention relates to the use of an ultraviolet fluorescence detector located in the drill string for determining the nature of the formations at the bottom of a wellbore to allow the drilling trajectory to be changed during drilling operations.

2. Background Art

When drilling it is important to know the nature of the formations located around the bottom of the well as it is drilled. By knowing the nature of the formations at the drill bit, is it possible to control the position of the drill bit and keep the well trajectory in the reservoir. Generally a well is drilled using a rotary drilling tool comprising a tubular drill string with a drill bit mounted at the end. A drilling fluid is supplied from the surface into the inside of the tubular drill string and pumped down to the drill bit where it is discharged into the wellbore, returning to the surface via the annular space between the drill string and the wellbore wall. The drilling fluid is used for the cooling and lubricating the drill bit and removing material cut away by the drill (cuttings) and for stabilizing the borehole during drilling.

Information regarding the drilling conditions can be obtained by measuring the properties of the drilling fluid, in particular the properties of the cuttings carried by the drilling fluid returning to the surface. One such property that can be measured is the presence of hydrocarbons in the drilling fluid. Detecting hydrocarbon fluorescence in the drilling fluid returning to the surface is known. Both U.S. Pat. No. 5,084,617 and U.S. Pat. No. 4,609,821 disclose detecting the presence of hydrocarbons in the drilling fluid cuttings. However, their analysis is performed once the drilling fluid with cuttings has returned to the surface. A problem with these methods is that, as the drilling depths can reach many hundreds of meters deep, there is a delay before the drilling fluid from the bottom of the well reaches the surface to be analysed and therefore the information the analysis it provides may no longer relate to the properties of the formations at the current location of the drill bit.

Being able to know as quickly as possible the nature of the formation at bottom of the wellbore is important so it is possible to alter the direction of the drill bit and enhance oil recovery by accurate well placement.

As the area where the drill bit can be several kilometers away from the surface, to determine what is happening at the area of the drill bit downhole techniques termed 'measurement-while-drilling' (MWD) and logging-while-drilling' (LWD) have been developed. These techniques involve placing sensors in the drill string to measure of variety of parameters which provide information on the nature of the wellbore and drilling process.

Currently measurements taken in known MWD and LWD techniques still take place some distance away from the drill bit location. Due to the mechanical vibrations and shocks of the drilling process and the lack of space near the drill bit it is difficult to place sensors close to the drill bit to preserve sufficient mechanical integrity. Therefore the measurements taken concern the formations at the level of the measuring devices and not the formations at the end of the drill bit. When the information regarding the properties of the formation reaches the surface, the drill bit can be some distance away from the formation where the measurements were taken.

U.S. Pat. No. 6,176,323 describes a drilling system with sensors to measure a variety of parameters. This document discloses measuring optical properties of the drilling fluid, using two sensors to determine whether native hydrocarbons are present in the drilling fluid. One sensor determines the properties of the drilling fluid in the drill string and a separate sensor determines the properties of the drilling fluid containing the cuttings returning to the surface.

GB2389380 describes a drilling system with sensors to determine the nature of the formations at the bottom of the well. The document discloses using at least two measuring means. One measuring means measures the properties of the drilling fluid inside the drill string and the second measuring means measures the properties of the drilling fluid outside the drill string, which is carrying the cuttings back up to the surface. The measuring means may measure electrical impedance, pH, nuclear density or electric voltage to determine the nature of the formations at the bottom of the well.

The invention proposes using an ultraviolet fluorescence detector that can receive drilling fluid from both inside and outside the drill string and can be located close to the drill bit. If the measurement can be taken close to the drill bit, information on the nature of the drill bit location can be received quickly and its path adjusted if necessary.

SUMMARY OF THE INVENTION

Accordingly one aspect of the invention provides an apparatus for determining the nature of the formation at the bottom of a wellbore being drilled with a tubular drill string through which drilling fluid is pumped to return the drilling fluid to the surface via the wellbore, the apparatus comprising: a tool body for installation in a drill string with a bore extending therethrough; and a sensor or detector for measuring a property of the drilling fluid in a passageway in the tool body; the passageway being configured to receive drilling fluid from inside the drill string and to receive drilling fluid from outside the drill string such that the drilling fluid can be directed past the sensor so as to enable measurements to be made.

The sensor is preferably an ultraviolet fluorescence detector.

The apparatus allows cuttings brought up by the drilling fluid to be examined, for example by using ultraviolet fluorescence, to detect the presence of oil and gas in the formation.

The drilling fluid from outside the drill string contains the cuttings formed by the drilling process. By performing differential measurements of the drilling fluid inside and outside the drill string, information about the drilled formation can be obtained.

The tool body comprises a first passageway extending from the outside of the drill string to the detector and a second passageway extending from the inside of the drill string to the detector from which the drilling fluids can flow so as to be diverted past the ultraviolet light detector.

The ultraviolet light detector comprises a light emitter and a fluorescence detector and a single passageway running past the emitter and detector which can receive drilling fluid obtained from the inside and outside of the drill string.

Preferably the apparatus also comprises a valve that is operable to divert drilling fluid into the detector from either inside the drill string or outside the drill string. This restricts the drilling fluid that flows through the detector to allowing either only drilling fluid from inside the drill string or only drilling fluid outside the drill string to flow through the detector. By diverting drilling fluid from inside the drill string through the ultraviolet light detector the drilling fluid that will not have cuttings in it can be used to normalize the measurement.

Preferably the tool body is located close to the drill bit so that the measurements of the properties for the drilling fluid outside the drill string can be can be made while the drill bit is still substantially in the same location as where the drilling fluid was discharged form the drill bit. As the drilling fluid flows at several centimeters per second if the measurement of the properties of the drilling fluid inside and outside the drill string are taken close to the drill bit you can receive information regarding the nature of the formations at the location of the drill bit quickly, as the drilling speed is substantially slower than the flow rate of the drilling fluids.

A second aspect of the invention is a method for determining the nature of the formation at the bottom of a wellbore being drilled with a tubular drill string through which drilling fluid is pumped to return to the surface via the wellbore the drill string comprising an ultraviolet fluorescence detector, the method comprising, directing a portion of a drilling fluid from inside the drill string past the detector and obtaining a first fluorescence measurement; directing a portion of a drilling fluid from outside the drill string past the detector and obtaining a second fluorescence measurement; and using the first and second fluorescence measurements to determine the nature of the formation at the bottom of the wellbore.

Preferably the method comprises using the first fluorescence measurement of the drilling fluid from inside the drill string to normalize the ultraviolet fluorescence detector. Preferably the method comprises operating a valve to divert drilling fluid from inside the drill string through the detector or to divert the flow of drilling fluid from outside the drill string through the detector.

In a particularly preferred embodiment the method comprises measuring the fluorescence near the drill bit. This enables information about the nature of the formations at the drill bit to be received quickly.

It is also preferred the method is preformed using the apparatus as described above.

DETAILED DESCRIPTION

Figure 1:
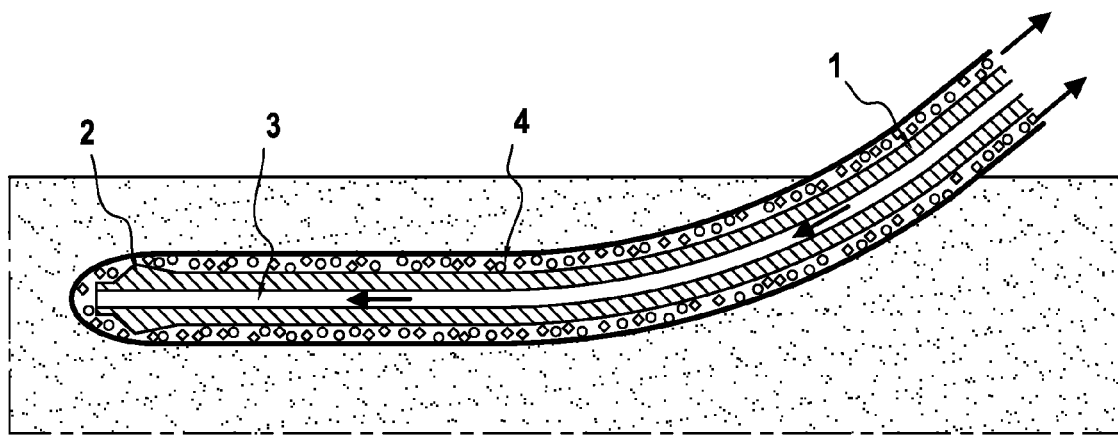
FIG. 1 shows a view of a drilling assembly in a wellbore.

With reference to FIG. 1 a drilling assembly comprises a tubular drill string 1 connected to a drill bit 2. During drilling, drilling fluid 3 is pumped through the tubular of the drill string 1 at a speed of about 1 m/s and is discharged from the drill bit 2. The drilling fluid collects the formation cuttings produced by the drilling at the well bottom and flows back to the surface via the annulus between the drill string 1 and the wall of the bore hole. The rate of penetration (ROP) of the drill bit 2 is about 1 m/h.

Figure 2:
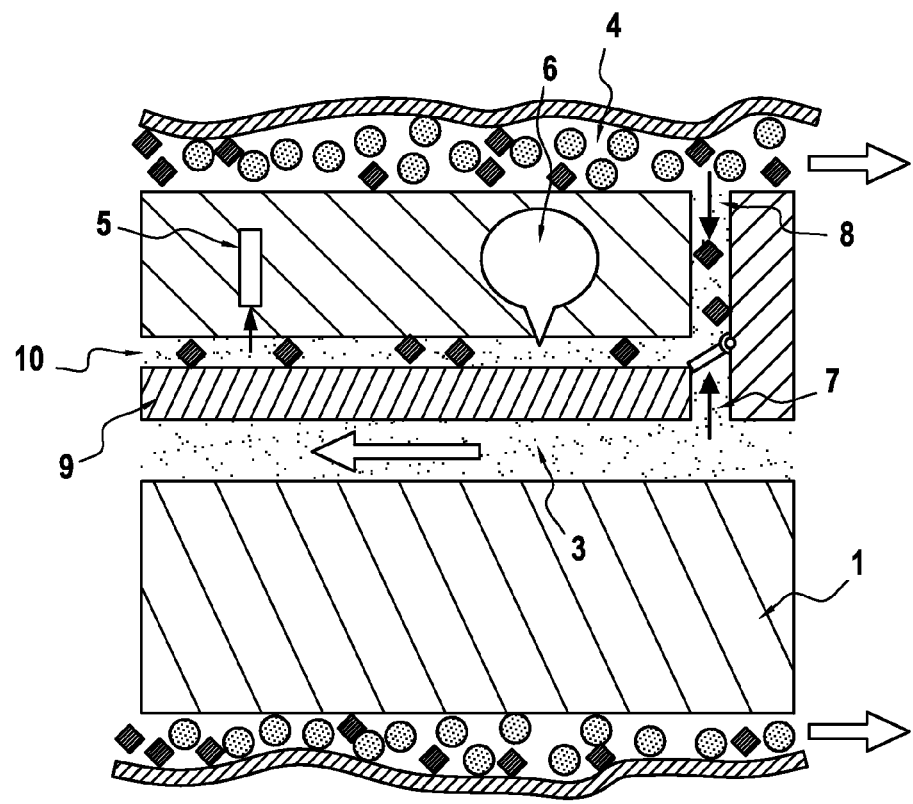
FIG. 2 shows a schematic view of a tool body with ultraviolet detector as part of the drill string for determining the nature of the formations around the borehole.

With reference to FIG. 2 an apparatus according to an embodiment of the invention comprises a fluorescence detector 5 and an ultraviolet light emitter 6. The detector is tuned to detect the presence of hydrocarbon fluorescence. The drilling fluid can be supplied to the detector by either passing through a passageway 7 leading from inside the drill string carrying 'clean' drilling fluid to the detector or can pass through a passageway 8 leading from the annulus between the drill string and wellbore wall carrying drilling fluid with cuttings 4. The type of drilling fluid that can flow to the detector is controlled by a valve 9 that diverts the required drilling fluid into the passageway 10.

According to the invention, the drilling fluid 3 is diverted from the inside of the drill string 1 into the passageways 7 and 10 that lead to the ultraviolet detector. The ultraviolet light detector will detect the fluorescence of the drilling fluid to provide a baseline value to normalize the measurements. A valve 9 is operated to stop drilling fluid 3 from inside the drilling string flowing through the detector and to allow drilling fluid with cuttings 4 from outside the drilling string into the passage 10. The drilling fluid with cuttings 4 flows past the ultraviolet light detector which will detect the fluorescence of the drilling fluid together with any hydrocarbons from the drilled cuttings. A differential measurement regarding the presence of hydrocarbons in the drilling fluid is thus obtained and provides information about the nature of the formations at the bottom of the drilling well. This data obtained from the detector is transmitted to the ground surface level via a data transmitter and receiver. The data is analysed at the ground surface level and this information can then be provided to the driller to alter the trajectory of the drill if necessary.

By locating the tool body containing the ultraviolet detector close to the drill bit the nature of the formation at the location of the drill bit at the current time can be obtained because the time between the drill bit cutting through a formation and the time at which the nature of the formations can be determined is small and the drill bit will not have not advanced very far.

The apparatus according to the invention can be placed in the drill string relatively close to the bit. For example, apparatus placed around 50 feet (~15 m) above the bit will 'see' cuttings around 15 seconds after they are drilled whereas the tool will not pass the location from which they came for another 15 hours. The exact positioning of the apparatus in the drill string may depend on other factors affecting the drill string design.

Using only one detector avoids variation in measurements due to different detection responses or variations in measurement geometry.

Changes may be made while still remaining within the scope of the invention. For example, the embodiment described above is founds as part of a relatively conventional rotary drilling setup. However, it could just as easily be part of a coiled tubing drilling setup (CTD) or as part of a wireline drilling system that can be used for drilling lateral wells from a main borehole or the like. Also, the fluorescence sensor describe above can be replaced or augmented with sensors for measuring other properties of the drilling fluid, especially properties that change when the cuttings contain oil.

What is claimed is:

1. An apparatus for determining the nature of the formation at the bottom of a wellbore being drilled with a tubular drill string through which drilling fluid is pumped to return the drilling fluid to the surface via the wellbore, the apparatus comprising:

a tool body for installation in a drill string with a bore extending therethrough; and a sensor for measuring a property of the drilling fluid in a passageway in the tool body;

the passageway being configured to receive drilling fluid from inside the drill string and to receive drilling fluid from outside the drill string such that the drilling fluid can be directed past the sensor so as to enable a first measurement to be made of the drilling fluid from only inside the drill string at a first time, and a second measurement to be made of the drilling fluid from only outside the drill string at a second time, wherein the first and second times are different.

2. The apparatus according to claim 1 wherein the sensor is an ultraviolet fluorescence detector.

3. The apparatus according to claim 1, comprising a first passageway extending from the outside of the drill string to the sensor and a second passageway extending from the inside of the drill string to the sensor through which the drilling fluids can flow so as to be directed past the sensor.

4. The apparatus according to claim 1, comprising a separate passageway in which the sensor is located to receive drilling fluid from outside the drill string or from inside the drill string.

5. The apparatus according to claim 1, wherein the tool body comprises a valve that is operable to divert drilling fluid to the sensor from either inside the drill string or outside the drill string.

6. A drilling apparatus, comprising:
   a tubular drill string with a drill bit located at a lower end thereof, and
   an apparatus as claimed in claim 1 being located in the drill string close to the drill bit so that measurements of drilling fluid outside the drill string can be made while the drill bit is still substantially in the same location as that in which the drilling fluid was discharged from the drill bit.

7. A method for determining the nature of the formation at the bottom of a wellbore being drilled with a tubular drill string through which drilling fluid is pumped to return to the surface via the wellbore, the drill string comprising an ultraviolet fluorescence detector for measuring a property of the drilling fluid, the method comprising the steps of:
   directing a portion of a drilling fluid from inside the drill string past the detector and obtaining a first measurement at a first time while preventing a portion of a drilling fluid from outside the drill string to be directed past the detector;
   directing a portion of a drilling fluid from outside the drill string past the detector and obtaining a second measurement at a second time while preventing a portion of a drilling fluid from inside the drill string to be directed past the detector; and
   using the first and second measurements to determine the nature of the formation at the bottom of the wellbore.

8. The method according to claim 7, further comprising the step of using the first measurement of the drilling fluid from inside the drill string to normalize the detector.

9. The method according to claim 7, further comprising the step of operating a valve to divert drilling fluid from inside the drill string past the detector or to divert the flow of drilling fluid from outside the drill string past the detector.

10. The method according to claim 7, further comprising the step of measuring the properties of the drilling fluid near the drill bit.

11. An apparatus for determining the nature of the formation at the bottom of a wellbore being drilled with a tubular drill string through which drilling fluid is pumped to return the drilling fluid to the surface via the wellbore, the apparatus comprising:
   a tool body for installation in a drill string with a bore extending therethrough;
   an ultraviolet fluorescence detector for measuring a fluorescence of the drilling fluid in a passageway in the tool body; and
   a valve positioned in the tool body operable to separately divert drilling fluid to the detector from either inside the drill string or outside the drill string so as to enable a differential measurement to be made.

* * * * *